United States Patent [19]
Rho et al.

[11] Patent Number: 5,856,511
[45] Date of Patent: Jan. 5, 1999

[54] SYNTHESIS OF 2-(2-FUROYL)-4(5)-(2-FURANYL)-1H-IMIDAZOLE AND ANALOGS THEREOF

[75] Inventors: Taikyun Rho, Saddle Brook; Michael E. Lankin, Cedar Grove; David H. Shih, Lawrenceville; Claire M. Lankin, Cedar Grove, all of N.J.

[73] Assignee: Alteon Inc., Ramsey, N.J.

Related U.S. Application Data

[60] Provisional application No. 60/024,673, Aug. 7, 1996.

[21] Appl. No.: 906,867

[22] Filed: Aug. 6, 1997

[51] Int. Cl.$^6$ .................................................. C07D 407/14
[52] U.S. Cl. .......................................................... 548/315.4
[58] Field of Search ........................................... 548/315.4

[56] References Cited

U.S. PATENT DOCUMENTS 4,665,192   5/1987   Cerami ..................................... 548/336

OTHER PUBLICATIONS

CA 126: 229620 Compositons and methods for elimination of advance glycosylation endproducts (in vivo), Mallon. Feb. 1997.

Arcorta et al., 1975, J. Het. Chem., 12:215.

Bucala et al., 1992, Advances in Pharmacology, 23:1–34.

Chang et al, 1985, J. Biol. Chem., 260:1970–4.

Dubac et al.,1991, Synth. Commun., 21:11.

Maillard et al., 1912, C.R. Acad. Sci., 154–66–8.

*Primary Examiner*—Joseph K. McKane
*Attorney, Agent, or Firm*—Klauber & Jackson

[57] ABSTRACT

The present invention relates to a practical and facile synthesis of 2-(2-furoyl)-4(5)-(2-furanyl)-1H-imidazole (FFI) and analogs thereof. The synthesis utilized a novel hydrazinium salt as an intermediate reaction product which facilitates the isolation of purified product in high yields.

4 Claims, No Drawings

SYNTHESIS OF 2-(2-FUROYL)-4(5)-(2-FURANYL)-1H-IMIDAZOLE AND ANALOGS THEREOF

This Application claims priority from U.S. Provisional Application 60/024,673, filed Aug. 7, 1996, the priority which is hereby claimed under 35 U.S.C. §119.

BACKGROUND OF THE INVENTION

The present invention relates the synthesis of 2-(2-furoyl)-4(5)-(2-furanyl)-1H-imidazole (FFI), and analogs thereof. FFI has been known for a number of years as a fluorescent chromophore formed as a result of the advanced glycosylation process.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Maillard, C. R. Acad. Sci., 154, pp. 66–68, (1912). Further studies have suggested that stored and heat treated foods undergo non-enzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin A1c. The reaction has also been found to occur with a variety of other body proteins, such as lens crystallins, collagen and nerve proteins. See, for instance, Bucala et al., "Advanced Glycosylation: Chemistry, Biology, and Implications for Diabetes and Aging," in Advances in Pharmacology, Vol. 23, pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In Cerami, U.S. Pat. No. 4,665,192, FFI was first identified and characterized. Various utilities for FFI have been proposed, among them, therapeutic methods which utilize FFI as an agent to induce macrophage stimulation, and thus accelerate the body's own process for removal of advanced glycosylation endproducts.

Necessary to such therapeutic methods is a ready and facile process for the chemical synthesis of FFI. Heretofore, preparation was by isolation from natural sources, or via the synthetic route proposed by Chang et al., J. Biol. Chem., 260, pp. 1970–1974 (1985). These methods suffer from poor yields and contaminating by-products which result in the use of difficult purification procedures. The present invention addresses such problems.

SUMMARY OF THE INVENTION

In accordance with the present invention, a facile and productive synthesis of FFI, and analogs thereof, is disclosed.

Thus, the present invention relates to a process for the preparation of FFI of the formula I

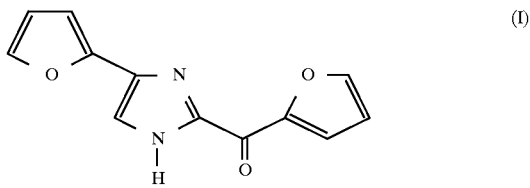

which comprises (a) reaction of a 2-haloacetyl compound of the formula II

wherein X is chloro, bromo or iodo, with 1,1-dialkylhydrazine of the formula III

wherein R and R' are each a lower alkyl group, to afford the compound of formula IV

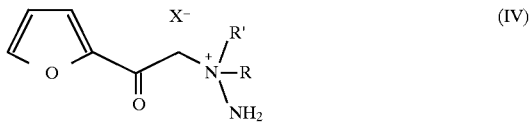

wherein R and R' are as hereinbefore defined; and (b) reaction of the compound of formula IV with methanol at reflux temperatures to afford the desired product of formula I.

Accordingly, it is a principal object of the present invention to provide a convenient and facile process for the preparation of 2-(2-furoyl)-4(5)-(2-furanyl)-1H-imidazole (FFI), and analogs thereof, using starting materials which are readily available.

It is a further object of the present invention to provide a process as aforesaid which minimizes by-product formation and thus affords the desired product in a relatively pure state, thus obviating the necessity for additional complicated purification procedures.

Other objects and advantages will become apparent to those skilled in the art from a consideration of the ensuing description.

DETAILED DESCRIPTION OF THE PREFERRED EMBODIMENT

In accordance with the present invention, disclosed is a process for the preparation of compounds of the following formula I

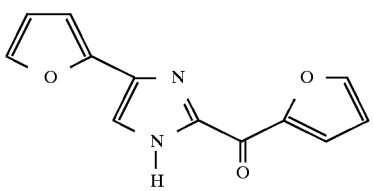 (I)

The process of the present invention thus relates to the preparation of FFI of the formula I which comprises the initial reaction of a 2-haloacetyl compound of the formula II

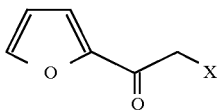 (II)

wherein X is chloro, bromo or iodo, with 1,1-dialkylhydrazine of the formula III

 (III)

wherein R and R' are each a lower alkyl group, to afford the compound of formula IV

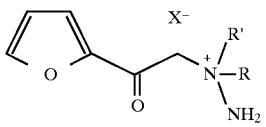 (IV)

wherein R and R' are as hereinbefore defined.

The lower alkyl groups referred to herein contain 1–6 carbon atoms and include methyl, ethyl, propyl, butyl, pentyl, hexyl, and the corresponding branched-chain isomers thereof.

The preparation of the 2-acetyl compounds of formula II are described in Dubac et al., *Synth. Commun.*, 1991, 21, p. 11, and Arcorta et al., *J. Het. Chem.*, 1975, 12, page 215. The 1,1-dialkylhydrazines of formula III are well-known in the art, and are commercially available, for instance, from the Alrich Chemical Co.

The reaction of the starting material of formula II with the 1,1-dialkylhydrazine of formula III is typically conducted in an anhydrous solvent. Typical solvents include ethyl ether, tetrhydrofuran, and the like. Reaction times vary from about 30 minutes to about 2 hours, depending upon the nature of the reactants. Typically, this step is conducted at temperatures ranging from about 0° to about 15° C.

In subsequent reaction step (b), the reaction product IV is contacted with methanol at reflux temperatures to afford the desired product of formula I. Typical reaction times for this step vary from 1 to 5 hours, depending upon the particular starting materials being utilized.

While not wishing to be bound by any mechanistic theory, it is believed that the subsequent step (b) results in a rearrangement illustrated by the following reaction scheme, resulting in the preparation of FFI in a facile manner.

In the following Scheme I, the reaction is illustrated using X=Br and R and R'=methyl Scheme I

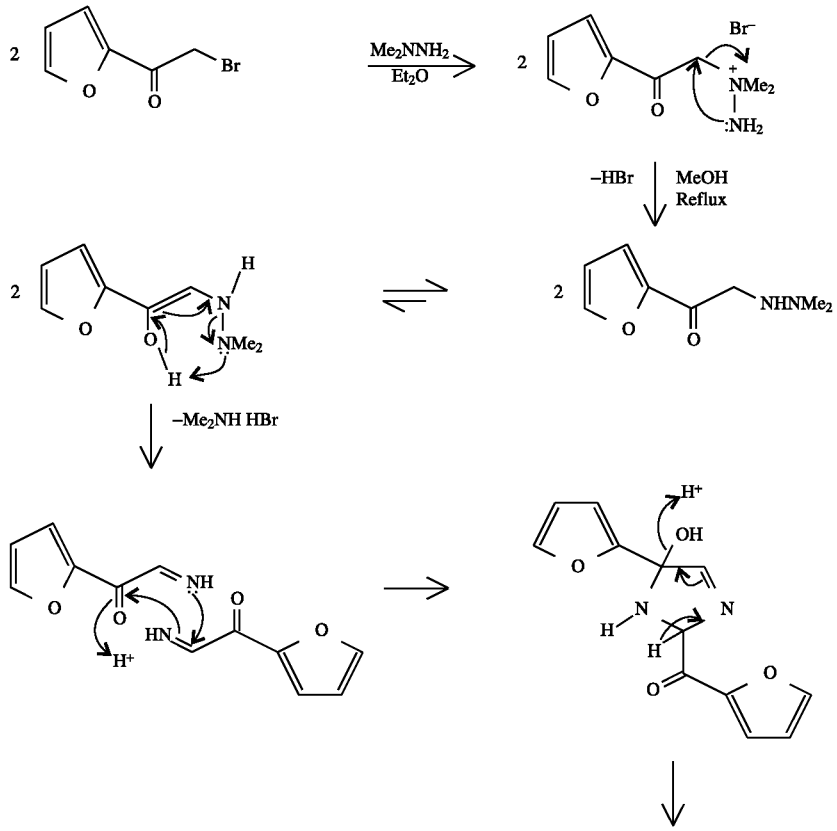

-continued
Scheme I

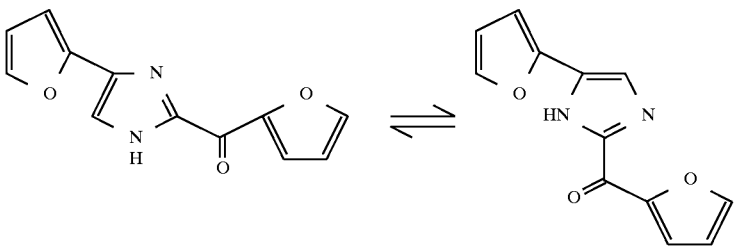

The FFI of formula I can be further converted to the corresponding alkyl, alkanoic acid, aryl and heteroaryl substituted compounds by reaction with the appropriate halide of the formula V

R"—X  (V)

wherein R" is an alkyl, alkanoic acid, aryl or heteroaryl group and X is chloro, bromo or iodo. Typically, this reaction is conducted in an anhydrous polar solvent such as dimethylformamide. Typical reaction times vary from 5 to about 12 hours, and reflux temperatures are generally preferred, depending upon the nature of the solvent. Where necessary, the R"—X reactant can contain a blocking group which is then removed in the final steps of the process to afford the desired compound.

The alkyl groups can contain from 1 to 10 carbon atoms. The alkanoic acid groups likewise can contain from w to 10 carbon atoms, with hexanoic acid being a preferred substituent.

Typical aryl groups include phenyl, and lower alkyl or lower alkoxy substituted phenyl groups.

The heteroaryl groups aforementioned contain from 4–7 ring members, and contain 1–3 heteroatoms, e.g., oxygen, nitrogen, or sulfur. Representatives of such heterocyclic groups are those such as pyridyl, methylpyridyl, imidazolyl, and pyrrolidinyl.

Representative compounds produced by the process of the present invention include:
2-(2-furoyl)-4(5)-(2-furanyl)-1H-imidazole (FFI);
4-(2'-furanyl)-2-(2'-furoyl)-1H-imidazole-1-hexanoic acid (FFI-HA); and
4-(2'-furanyl)-2-(2'-furoyl)-1H-imidazole-1-butyric acid (FFI-BA).

The present invention will be better understood from a consideration of the following examples, which describe the preparation of compounds according to processes illustrative of the present invention. It will be apparent to those skilled in the art that many modifications, both of materials and methods, may be practiced without departing from the purpose and intent of this disclosure.

EXAMPLES

Preparation of Starting Materials

Example A

2-Bromoacetylfuran

To a 5 liter round bottomed flask is added 2-acetylfuran (440 grams, 4 moles) and 2.4 liters of ethyl ether at 5 C in an ice bath. To this solution is added, dropwise over a period of two hours, with vigorous stirring, 230 mL bromine (713 grams, 4.46 moles). After the bromine addition is complete, the reaction mixture is stirred for an additional two hours, and then quenched with the addition of 300 mL of water. The mixture is then allowed to separate overnight, and the ether layer is washed with water (3×300 mL), dried over magnesium sulfate, and filtered. Removal of the solvent affords the title product having $^1$H-NMR (CDCl$_3$) delta 7.53 (t, 1J, J=0.72 Hz), 7.21 (d, 1H, J=3.68 Hz), 6.46 (dd, 1H, J=3.66 Hz and 1.48 Hz), 4.20 (s, 2H). $^{13}$C (CDCl$_3$ 189.22, 150.12, 147.61, 119.42, 112.93, 30.46 ppm.

Alternately, the title compound can be utilized in the ether solution in further reactions.

Preparation of Compounds of Formula I

Example 1

2-(2-Furoyl)-4(5)-(2-furanyl)-1H-imidazole

A. In a 5 liter round bottomed flask equipped with a mechanical stirrer and an addition funnel, is placed 2-bromoacetylfuran (560 g, 2.95 mol, assumed 75% from acetylfuran in ether (3,2 L)). The solution is cooled to 5° C. in an ice bath and 1,1-dimethyl hydrazine (178 g, 2.96 mole) is added dropwise over a period of one and one-half hours. As the hydrazine is added, a yellow solid begins to precipitate out and the reaction mixture becomes very thick. After the addition is completed, the mixture is stirred an additional hour and allowed to stand for an additional two hours. The off-white solid is collected and dried under vacuum for three days to afford 1,1-dimethyl-1-(2'-furoyl)hydrazinium bromide (720 g, 72% yield), having a melting point of 134°–135° C. $^1$H-NMR (DMSO-d$_6$) δ 8.18 (1H, d, J=0.72 Hz), 7.77 (1H, d, J=3.64 Hz), 6.85 (1H, dd, J=3.64 Hz and 1.45 Hz). $^{13}$C (DMSO-d$_6$) 179.16, 150.65, 150.31, 122.19, 113,84, 688.81, 56.94 ppm.

B. To a 5 liter round bottomed flask is added the hydrazinium bromide produced in step (a) detailed in the foregoing paragraph (300 g, 1.2 mole) and methanol (2.4 L). The solids slowly dissolve as the mixture is heated to reflux temperatures. The reaction mixture is then refluxed for three hours, whereupon most of the methanol is removed in vacuo. The resultant oil is poured onto ice water (1.5 L) and the aqueous mixture is stirred overnight. The brown solid is collected and recrystallized from methanol/ether to afford the 2-(2-furoyl)-4(5)-(2-furanyl)-1H-imidazole title product as yellow crystals (85 g, 62% yield), having identical properties to those reported in the literature.

Example 2

A. To a 100 mL round bottom flask was added FFI (3.0 g, 13.2 mmol)D and dry DMF (45 mL) under nitrogen. Sodium hydride (475 mg, 19.8 mmol) was added to the reaction mixture. This mixture was stirred at 90° C. and ethyl 6-bromohexanoate (3.24 g, 14.5 mmol) was added. The reaction mixture was stirred at 90° C. for 10 hours under nitrogen. After removing the solvent by high vacuum distillation, the dark reddish oil was recrystallized from tert-butyl methyl ether to give ethyl 4-(2'-furanyl)-2-(2'-furoyl)-1H-imidazole-1-hexanoate, as a yellow crystal 2.0 g (41%); mp 65°–66° C. 1H-NMR (CDCl3) δ 8.18 (1H, d, J=3.68 Hz), 7.71 (1H, m), 7.41 (1H, m), 7.34 (1H, s), 6.72 (1H, d, J=3.28 Hz), 6.61 (1H, dd, J=3.5 Hz and 1.65 Hz), 6.47 (1H, dd, J=3.28 Hz and 1.84 Hz), 4.47 (2H, t, J=7.32 Hz), 4.11 (2H, q, J=7.32 Hz), 2.29 (2H, t, J=7.52 Hz), 1.90 (2H, m), 1.68 (2H, t, J=7.32 Hz), 1.40 (2H, m), 1.23 (3H, t, J=7.34 Hz). 13C-NMR (CDCl3) 173.5, 170.2, 151.3, 149.2, 147.6, 141.6, 141.1, 134.5, 123.7, 121.6, 112.6, 111.4, 105.4, 60.3, 48.9, 34.1, 30.9, 26.1, 24.5, 14.3 ppm. Anal. Calcd for $C_{20}H_{22}N_2O_5$: C, 68.45; H, 5.99; N, 7.54. Found C, 64.56; H, 5.95; N, 7.40.

B. To a 250 mL round bottomed flask was placed the ethyl ester prepared as detailed in the above paragraph A (1.0 g, 2.7 mmol), methanol (20 mL) and barium hydroxide monohydrate (0.56 g, 3 mmol). The mixture was stirred for 40 hours at room temperature. Solids were filtered off, and the filtrate was concentrated in vacuo to give a yellow oil. To the oil was added water (20 mL), and PH was adjusted to 4 by adding 6N HCl in an ice bath. The aqueous layer was extracted with methylene chloride (2×20 mL). The organic layers were combined and evaporated in vacuo to give a yellow solid. The solid was recrystallized from chloroform/hexane to give 4-(2'-furanyl)-2-(2'-furoyl)-1H-imidazole-1-hexanoic acid as a off-white crystal (0.82 g, 84%); mp 105°–106° C. $^1$H-NMR (CDCl$_3$) δ 8.18 (1H, d, J=3.68), 7.71 (1H, m), 7.41 (1H, m), 7.35 (1H, s), 6.72 (1H, d, J=3.28 Hz), 6.60 (1H, dd, J=3.5 Hz and 1.65 Hz), 6.47 (1H, dd, J=3.28 Hz and 1.84 Hz), 4.47 (2H, t, J=7.32 Hz), 2.36 (2H, t, J=7.32 Hz), 1.89 (2H, m), 1.69 (2H, m). $^{13}$C-NMR (CDCl$_3$) 179.2, 170.3, 151.3, 149.2, 147.4, 141.6, 14.2, 134.5, 123.8, 121.6, 112.6, 111.5, 105.4, 48.9, 33.8, 30.9, 26.0, 24.1 ppm.

Example 3

A. To a 250 mL round bottomed flask was placed FFI (5.0 g, 22 mmol) and dry DMF (100 mL) under dry N$_2$ atmosphere. To the mixture was added sodium hydride (60%. 1.0 g, 25 mmol) and stirred for 15 minutes. 1,6-Dibromohexane (11.0 g, 45 mmol) was added all at once. The mixture was heated to 85° C. and stirred for 14 hours. The solvent was removed by high vacuum distillation. To the oily residue was added water (100 mL) and extracted with chloroform (80 mL×3). The organic layer was washed with water (50 mL) and dried over anhydrous MgSO$_4$. The unreacted dibromohexane was removed by flash chromatography over TLC grade silica gel (100 g) with chloroform/hexane (1:1). Upon evaporation of the solvent, 5.5 g of 4-(2'-Furanyl)-2-(2'-furoyl)-1H-1-(6'-bromohexyl)imidazole, as a yellow oil (65%), was obtained. $^1$H-NMR (CDCl$_3$) δ 8.17 (1H, d, J=3.28 Hz), 6.59 (1H, dd, J=3.5 Hz and 1.65 Hz), 6.46 (1H, dd, J=3.27 Hz and 1.85 Hz), 4.45 (2H, t, J=7.3 Hz), 3.36 (2H, t, J=7.3 Hz), 1.86 (4H, m), 1.49–1.35 (4H, m). $^{13}$C-NMR (CDCl$_3$) 170.3, 151.4, 149.2, 147.7, 141.6, 141.2, 134.5, 123.8, 121.6, 112.6, 111.5, 105.4, 49.0, 33.7, 32.6, 31.1, 27.7, 25.8 ppm.

B. Bromohexyl-FFI (5.0 g, 12.8 mmol) and sodium azide (0.9 g, 13.8 mmol) were dissolved in the mixture of methanol (50 mL) and water (100 mL). The mixture was refluxed for 12 hours and extracted with chloroform (2×100 mL). The organic layer was washed with water (50 ML) and dried over anhydrous MgSO$_4$. After removing the solvent, 3.2 g of 4-(2'-furanyl)-2-(2'-furoyl)-1H-1-(6'-azidohexyl)imidazole, as a yellow oil, was obtained. $^1$H-NMR (CDCl$_3$) δ 8.17 (1H, d, J=3.67 Hz), 7.70 (1H, t, J=0.74 Hz), 7.40 (1H, m), 7.33 (1H, s), 6.71 (1H, d, J=3.28 Hz), 6.60 (1H, dd, J=3.5 Hz and 1.65 Hz), 6.46 (1H, dd, J=3.27 Hz and 1.85 Hz), 4.45 (2h, t, j=7.3 Hz), 3.32 (2H, t, J=7.3 Hz), 3.32 (2H, t, J=7.3 Hz), 1.86 (2H, m) 1.57 (2H, m), 1.39 (4H, m). $^{13}$C-NMR (CDCl$_3$) 170.3, 151.3, 149.2, 147.7, 141.6, 141.2, 134.5, 123.8, 121.6, 112.6, 111.5, 105.4, 51.3, 49.0, 31.1, 28.7, 26.3, 26.1 ppm.

C. To a 250 mL round bottom flask was added the azide (0.5 g, 1.4 mmol), tetrahydrofuran (THF) (150 mL), water (50 mL) and triphenyl phosphine (0.37 g, 1.4 mmol). The mixture was stirred for 14 hours and solvent was removed in vacuo. To the residue was added 20 mL of water and extracted with chloroform (2×20 mL). After flash chromatography over tlc grade silica gel (50 mL), 0.32 g of 4-(2'-furanyl)-2-(2'-furoyl)-1H-1-(6'-aminohexyl)imidazole, as a pure oil, was obtained. $^1$H-NMR (CDCl$_3$) δ 8.17 (1H, d, J=3.67 Hz), 7.71 (1H, t, J=0.74 Hz), 7.41 (1H, m), 7.33 (1H, s), 6.71 (1H, d, J=3.28 Hz), 6.60 (1H, dd, J=3.5 Hz and 1.65 Hz), 6.46 (1H, dd, J=3.27 Hz and 1.85 Hz), 4.34 (2H, t, J=7.3 Hz), 3.48 (2H, br s),), 2.68 (2H, m), 1.74 (2H, br s), 1.17 (4H, br s).

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A process for the preparation of 2-(2-furoyl)-4(5)-(2-furanyl)-1H-imidazole of the formula I

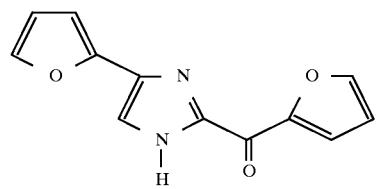

which comprises (a) reaction of a 2-haloacetyl compound of the formula II

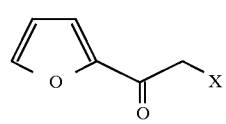

wherein X is chloro, bromo, or iodo; with 1,1-dimethylhydrazine of the formula III

wherein R and R' are lower alkyl groups, to afford the compound of formula IV

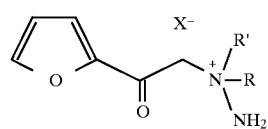

wherein R and R' are as hereinbefore defined;

(b) reaction of the compound of formula IV with methanol at reflux temperatures to afford the desired product of formula I.

2. The process of claim 1 wherein R and R' are both methyl groups.

3. The process of claim 1 wherein X is bromo.

4. The process of claim 1 which further includes reaction of the 2-(2-furoyl)-4(5)-(2-furanyl)-1H-imidazole with R"—X to produce the substituted-FFI compound, wherein R" is an alkyl, alkanoic acid, aryl or heteroaryl group and X is chloro, bromo, or iodo.

* * * * *